United States Patent
Tuohey et al.

(10) Patent No.: US 12,397,298 B2
(45) Date of Patent: Aug. 26, 2025

(54) REINFORCED COMPONENT FOR CELL CULTIVATION BIOREACTOR

(71) Applicant: Global Life Sciences Solutions USA LLC, Marlborough, MA (US)

(72) Inventors: Colin Tuohey, Marlborough, MA (US); Ralph Stankowski, Marlborough, MA (US)

(73) Assignee: Global Life Sciences Solutions USA, LLC, Marlborough, MA (US)

( * ) Notice: Subject to any disclaimer, the term of this patent is extended or adjusted under 35 U.S.C. 154(b) by 839 days.

(21) Appl. No.: 17/626,969

(22) PCT Filed: Jun. 30, 2020

(86) PCT No.: PCT/EP2020/068356
§ 371 (c)(1),
(2) Date: Jan. 13, 2022

(87) PCT Pub. No.: WO2021/008867
PCT Pub. Date: Jan. 21, 2021

(65) Prior Publication Data
US 2022/0258166 A1 Aug. 18, 2022

Related U.S. Application Data

(63) Continuation of application No. 16/513,491, filed on Jul. 16, 2019, now abandoned.

(51) Int. Cl.
*B01L 3/00* (2006.01)
*B01L 7/00* (2006.01)
(Continued)

(52) U.S. Cl.
CPC ............... *B01L 3/561* (2013.01); *B01L 3/505* (2013.01); *B01L 7/00* (2013.01); *C12M 23/14* (2013.01);
(Continued)

(58) Field of Classification Search
CPC .. B01L 3/561; B01L 3/505; B01L 7/00; B01L 2200/0684; B01L 2200/147;
(Continued)

(56) References Cited

U.S. PATENT DOCUMENTS 5,941,635 A 8/1999 Stewart
6,599,012 B2 7/2003 Gul
(Continued)

FOREIGN PATENT DOCUMENTS

CN 102481408 A 5/2012
CN 106715674 A 5/2017
(Continued)

OTHER PUBLICATIONS

"Industrial measurement Measuring Controlling Regulating 2011," Jan. 1, 2011, https://www.greisinger.de/files/upload/en/downloads/Catalogue_2011-01_english.pdf, 5 pages.
(Continued)

*Primary Examiner* — Michael L Hobbs
(74) *Attorney, Agent, or Firm* — CM Law; Jeff B. Vockrodt

(57) ABSTRACT

The present invention relates to a bioprocess bag 118 comprising a bag wall defining an enclosed volume for holding biomaterials. The bag wall comprises at least one inlet port 142 and at least one outlet port 146. The bioprocess bag 118 also comprises a tube structure 400 comprising a first opened-end proximate the bag wall and a second distal end, the tube extending into the enclosed volume, and the tube structure 400 comprising a reinforced portion 402 proximate the first opened-end.

18 Claims, 7 Drawing Sheets

(51) Int. Cl.
*C12M 1/00* (2006.01)
*C12M 1/34* (2006.01)

(52) U.S. Cl.
CPC ............ *C12M 23/26* (2013.01); *C12M 29/00* (2013.01); *C12M 41/12* (2013.01); *B01L 2200/0684* (2013.01); *B01L 2300/0609* (2013.01); *B01L 2300/0627* (2013.01); *B01L 2300/0832* (2013.01); *B01L 2300/18* (2013.01); *B01L 2400/0475* (2013.01)

(58) Field of Classification Search
CPC ..... B01L 2300/0609; B01L 2300/0627; B01L 2300/0832; B01L 2300/18; B01L 2300/123; B01L 2400/0475; C12M 23/14; C12M 23/26; C12M 23/28; C12M 29/00; C12M 41/12; C12M 37/00
See application file for complete search history.

(56) References Cited

U.S. PATENT DOCUMENTS

| | | | |
|---|---|---|---|
| 7,629,167 B2 | 12/2009 | Hodge et al. | |
| 9,109,193 B2 | 8/2015 | Galliher et al. | |
| 9,550,969 B2 | 1/2017 | Chotteau et al. | |
| 9,550,972 B2 | 1/2017 | Jeong et al. | |
| 9,566,385 B2 | 2/2017 | Franks | |
| 2003/0226857 A1* | 12/2003 | Bibbo | B01F 23/53 422/1 |
| 2012/0244609 A1* | 9/2012 | Selker | C12M 29/06 435/295.1 |
| 2014/0011270 A1 | 1/2014 | Chotteau et al. | |
| 2019/0031995 A1 | 1/2019 | Arnold et al. | |

FOREIGN PATENT DOCUMENTS

| | | |
|---|---|---|
| EP | 2503320 A2 | 9/2012 |
| JP | 2007282629 A | 11/2007 |
| JP | 2012527972 A | 11/2012 |
| JP | 2016537983 A | 12/2016 |
| JP | 2018183887 A | 11/2018 |
| WO | 2009093995 A1 | 7/2009 |
| WO | 2010138612 A2 | 12/2010 |
| WO | 2015077663 A1 | 5/2015 |
| WO | 2019067966 A1 | 4/2019 |

OTHER PUBLICATIONS

"Lemo 5-pin single notch female socket," https://www.alibaba.com/product-detail/Lemo-5-pin-single-notch-female_62572101832.html, Dec. 15, 2020, 10 pages.
Search Report received in International Application No. PCT/EP2020/068356 dated Jan. 19, 2021, 7 pages.
Thermo Scientific: "Thermo ScientificHyPerforma Single Use Bioreactor (S.U.B.)", Dec. 1, 2016, http://tools.thermofisher.com/content/sfs/brochures/UsersGuide2-1HyPerformaBioreactorSingle-UseDOC0014CDecember2016.pdf, 2 pages.
Written Opinion received in International Application No. PCT/EP2020/068356 dated Jan. 19, 2021, 14 pages.
Office Action received in Japanese Application No. 2022-502527 dated May 27, 2024, with translation, 7 pages.
Office Action received in Chinese Application No. 202080051284.0 dated Mar. 31, 2025, with translation, 15 pages.

* cited by examiner

REINFORCED COMPONENT FOR CELL CULTIVATION BIOREACTOR

FIELD OF THE INVENTION

The present invention relates to a novel bioprocess bag for cell cultivation having reinforced internal structures. More specifically, the invention relates to an improved bioprocess bag and related structures, including reinforced and improved tube features.

BACKGROUND OF THE INVENTION

Cell therapy is a new but rapidly expanding field in biotechnology which involves the administration of autologous or allogeneic cells that carry out a therapeutic effect in vivo. Cell therapy involves a number of mandatory stages from cell collection to cell injection into a patient. Cell culturing for cell therapy is carried out in clean room environment. Cell culturing and clean rooms has many mandatory regulations like particle size and count in clean room, number of patient samples handled at a time, and number of instruments per suite, as well as a requirement for a sterile environment etc.

Earlier systems for cell culture were stand alone, required large space and could not handle multiple patient samples at same time. Procedures for cell culturing for cell therapy involve a lot of human intervention, which may contaminate cell cultures and damage cell growth, especially small size cell cultures.

Disposable bioreactor or fermenter bags have been developed for cell therapy. The use of disposable bioreactor bags in cell culture reduces batch changeover times by eliminating time consuming cleaning and equipment validation, resulting in higher throughput. FIG. 1 shows a disposable bioreactor system described in U.S. Pat. No. 9,109,193, entitled "Continuous Perfusion Bioreactor System." FIG. 1 is more fully described in the '193 patent, and is described briefly herein. Certain aspects include an apparatus 100 including a vessel 114, which, in the illustrated embodiment, is a reusable support structure (e.g., a stainless steel tank) that surrounds and contains a container 118. Apparatus 100 can optionally include an environmental containment enclosure 120, which surrounds a portion of vessel 114. The container 118 may be configured as a collapsible bag (e.g., a polymeric bag). The collapsible bag 118 may be fluid tight to enable it to contain a liquid 122, which may contain reactants (e.g., certain solid objects), media, and/or other components necessary for carrying out a desired process such as a chemical, biochemical and/or biological reaction. Collapsible bag 118 may also be configured such that liquid 122 remains substantially in contact only with the collapsible bag during use and is not in contact with support vessel 114, so that the support structure can be reused without cleaning.

Also shown in FIG. 1 are an optional inlet port 142 and optional outlet port 146, which can be formed in container 118 and/or reusable support structure 114 and can facilitate convenient introduction and removal of a liquid and/or gas from the container. These ports may be positioned in any suitable location with respect to container 118. For instance, for certain apparatuses including spargers, the container may include one more gas inlet port located at a bottom portion of the container. Tubing may be connected to the inlet and/or outlet ports to form, e.g., delivery and harvest lines, respectively, for introducing and removing liquid from the container. One or more connections 164 may be positioned at a top portion of container 118 or at any other suitable location. Connections 164 may include openings, tubes, and/or valves for adding or withdrawing liquids, gases, and the like from container 118, each of which may optionally include a flow sensor and/or filter (not shown). Optionally, connections 164 may be in fluid communication with gas introduction and withdrawal ports 165.

For systems including multiple spargers, control system 134 may be operatively associated with each of the spargers and configured to operate the spargers independently of each other. Support structure 114 and/or container 118 may also include, in some embodiments, one or more ports 154 that can be used for sampling, analyzing (e.g., determining pH and/or amount of dissolved gases in the liquid), or for other purposes. These ports may be aligned with one or more access ports 156 of optional environmental containment enclosure 120.

Apparatus 100 may include, in some embodiments, one or more connection ports 180 for interconnecting an interior of reusable support structure 114 (e.g., gap 132) to an interior of a second apparatus. Additionally, or alternatively, the apparatus may include one or more connection ports 182 adapted for connecting an interior of container 118 (e.g., interior 56) to an interior of an interior of the second apparatus. These ports can facilitate transfer of a material from interior 56 to the second apparatus or to another suitable container (e.g., a sealed bag). Transfer may be accomplished, for example, by pumping the material through tubing (e.g., by peristaltic pumping or by applying a positive pressure to an inlet), by use of gravity, and/or by application of a vacuum.

Apparatus 100 may optionally include a mixing system such as an impeller 151 positioned within container 118, which can be rotated (e.g., about a single axis) using a motor 152 that may be external (or internal) to the container. The mixing system can be controlled by control system 134. Optionally, the container and/or support structure may include a utility tower 150, which may be provided to facilitate interconnection of one or more devices internal to the container and/or support structure with one or more pumps, controllers, and/or electronics (e.g., sensor electronics, electronic interfaces, and pressurized gas controllers) or other devices. Such devices may be controlled using a control system 134.

FIG. 2 shows another disposable bioreactor system described in U.S. Pat. No. 7,629,167 filed Jun. 6, 2005 and entitled "Disposable Bioreactor System and Methods." FIG. 2 is more fully described in the '167 patent, and is described briefly herein. As shown, the bioreactor 200 includes one or more ports 202 which may be used to add or withdraw gases and/or fluids from the bioreactor. A harvest or drainage port 204 is generally provided at the bottom of the bag so that gravity may be used to direct the contents out of the bioreactor. The probes and/or sensors 206 may be integral with a side of the bioreactor, such that the sensors and/or probes may be disposable as well. In one embodiment of the invention, the sensors/probes may be optical probes which present the output in a visual manner. Thus, the sensor/probe ports 206 may be used to visually monitor the status of the sensor/probe.

Integral with the bioreactor may be one portion of the mixing system. Specifically, as shown in FIG. 2, the portion of the mixing system included with the bioreactor may include one portion 208 of the mixing system—an impeller plate and impeller hub. The impeller plate connects to the drive system of the motor to power the impeller, and also provides a seal between the motor and the interior of the bioreactor. Some embodiments of the invention provide one or more exceptional mixing systems, which provides the system with an inexpensive method for providing agitation to the contents of the bioreactor. Such mixing systems may utilize materials such as HDPE (high-density polyethylene) and/or other gamma-irradiatable, biocompatible plastics. One or more components of the mixing system may be manufactured by machining blocks of material, but may also be molded and/or cast.

FIG. 3 shows another disposable bioreactor system described in U.S. Pat. No. 9,550,969 entitled "Flexible Bag for Cultivation of Cells." FIG. 3 is more fully described in the '969 patent, and is described briefly herein. As shown, an inflatable bioreactor bag 1 for cell cultivation comprises a top sheet 2 and a bottom sheet 3 of flexible material, joined together to form two end edges 4 and two side edges 5, wherein one baffle 6 or a plurality of baffles 6 extend from the bottom sheet 3 in a region of the bottom sheet 3 where the shortest distance to any one of the two end edges 4 (i.e. the closest end edge) is higher than about one fourth of the shortest distance D between the two end edges 4. The bag may be generally rectangular, in which case the shortest distance to any one (the closest one) of the end edges 4 will never be higher than D/2 for any point on the bottom sheet 3. Hence, the baffles 6 may extend from the bottom sheet 3 in a region where the shortest distance to the end edges 4 is between about one fourth and one half of the shortest distance D between the end edges 4, i.e. between D/4 and D/2.

The bag 1 may be pivotally mounted to a base 9 about a movable axis 7 generally parallel to the end edges 4. The movable axis 7 may be located below the bag 1 and the bag may be mounted on a support 8, e.g. with the distance between each edge 4 to the projection of the movable axis 7 on the bottom sheet 3 being approximately equal to D/2. Suitable pivotable supports mounted on a movable axis can be e.g. the WAVE Bioreactor™ Systems (GE Healthcare). The flexible material of the top 2 and bottom 3 sheets may be a polymeric material, such as a plastic film or laminate with a thickness e.g. in the 50-500 micron range. A laminate may in addition to one or more polymeric materials comprise e.g. bather layers, which may be polymers or inorganic oxides or metals. The top sheet 2 in particular can be transparent to ensure visibility into the bag. The top sheet 2 and the bottom sheet 3 are defined with respect to the positions during use of the bag, i.e. in use the top sheet 2 is located above the bottom sheet 3. The top and bottom sheets may also be distinguished in that the ports 11 are preferably located on the top sheet 2, providing a smooth outer surface of the bottom sheet 3, suitable for resting on the support 8. The side edges 5 may be longer than the end edges 4.

An advantage of the central location of the baffles 6 is that when the bag is partially filled with a cell suspension, inflated and rocking around the axis 7, essentially all the cell suspension will repeatedly pass by the baffles. This increases the agitation intensity and improves the gas exchange in the air-liquid interface, while the agitation is still mild enough not to cause any damage to the delicate cells.

In some embodiments, at least one of the baffles 6, such as two baffles, is/are tubular. One advantage of this is that the baffles can be made flexible enough to allow for easy packing and storage of the collapsed bags before use, but rigid enough to sustain the hydrodynamic forces during operation of the bag. A further advantage is that the tubular structure allows for transport of materials through the baffle into or out of the bag. Tubular baffles can e.g. be prepared from elastomeric materials that allow collapse of the structure during packing of the bag but are resilient enough to give complete recovery of the open tubular shape when the bag is filled and/or inflated. The elastomeric material can e.g. be a cross-linked silicone rubber or other vulcanized rubber material. If tubing with thick walls and/or high rigidity is used, the tubular baffles may also act as columns, keeping the top and bottom sheets of the bag separated before and during inflation of the bag.

A need remains for improved bioreactor or fermenter bags that are capable of withstanding sterilization, packaging, shipping, setup, and use.

SUMMARY OF THE INVENTION

The present invention includes aspects relating to an improved bioprocess bag and related structures, including reinforced and improved tube features. In one aspect, the invention relates to an improved bioprocess bag including a bag wall defining an enclosed volume for holding biomaterials, the bag wall comprising at least one inlet port and at least one outlet port; and a tube structure comprising a first opened-end proximate the bag wall and a second distal end, the tube extending into the enclosed volume, and the tube structure comprising a reinforced portion proximate the first opened-end. The reinforced section may include a pattern of sections that are raised relative to the tube outer surface, and the raised sections contacting each other when the tube structure is bent. The contact may prevent crimping of the tube structure during shipping, setup or operation.

In another aspect, the invention relates to a bioprocess bag including a bag wall defining an enclosed volume for holding biomaterials, the bag wall comprising at least one inlet port and at least one outlet port; and a tube structure comprising a first opened-end proximate the bag wall and a second closed-end distal to the bag wall, the tube extending into the enclosed volume, the tube structure comprising a predominantly cylindrical inner wall and a notch that extends at least a portion of the length of the inner wall, wherein the notch defines a channel that allows air to flow out when a probe is inserted into the tube structure.

These aspects of bioprocess bags may include other features used in mixers, bioreactors, and other relevant applications. Those features may include impellers, heaters, and gas outlets. The tube structure may be adapted to accept a probe, such as one having a thermocouple or resistance temperature detector (RTD). Alternatively, or in addition, the tube structure may be adapted to accept a sparging wand. It is contemplated that any number of tube structures according to embodiments of the present invention may be used together, or in combination with other tube structure in a single bioprocess bag. The tube structure may include a predominantly cylindrical inner wall, and a notch extending at least a portion of the length of the inner wall. The notch can be adapted to define a channel that allows air to flow out when a probe is inserted into the tube structure.

In one aspect, the invention includes a reinforced probe housing, the probe housing comprising; a tip portion having a first outer diameter and an first inner diameter defining a thickness, the inner diameter adapted to accept a probe, the probe housing having a closed-end proximate the tip portion; a reinforced portion sharing the same inner diameter as the tip portion, wherein the outside diameter of the reinforced portion includes raised sections that provide reinforcement through contact with one another when the probe housing is bent, the probe housing having an opened-end proximate the reinforced portion, the opened-end adapted to accept the probe. The reinforced probe housing can be included with a bioprocess bag or used independently. The probe housing may be adapted to receive a thermocouple or resistance temperature detector (RTD).

DETAILED DESCRIPTION

The present inventors have found that several of the internal structures of a bioreactor or fermenter bag are susceptible to damage or perceived damage as a result of sterilization and packaging, and further damage to these elements can occur during shipping, setup, or use. The sterilization of the bag with gamma irradiation can in some cases exacerbate the problem by fusing adjacent pieces of material or freezing the material into bent shape. With respect to parts that are internal to the bag, these problems are sometimes compounded by the inability to inspect internal portions of the bag given the need to maintain sterility and not compromise the bag structure. The perception of damage to an internal part may result in the entire bag being deemed unsuitable for use. The tube structure maybe adapted to accept a probe, such as a thermocouple or resistance temperature detector (RTD), or a sparging wand. Alternatively, or in addition, the tube structure may be adapted for introducing or withdrawing material from the bioprocess bag.

Those internal bioreactor bag structures most susceptible to this kind of damage or perceived damage are tubular structures. These tubular structures internal to the bag may become bent, crimped, folded at some point in the supply chain.

One particular structure that is susceptible to damage is the thermowell tube found in existing bioreactor bags. One example of such a thermowell is described in U.S. Pat. No. 6,599,012 entitled "Thermowell Adapter," which is incorporated by reference for its disclosure of thermowell structures. The thermowell tube is a piece of straight tubing made from plastic material that allows insertion of a thermowell into a bioreactor bag without breaching the seal of the bag. Often the thermowell is made from a molded plastic or rubber material. A rigid insert is used to prevent tubing from collapsing and self-sealing internally during gamma irradiation. In some cases, the rigid support breaks and can puncture the tubing. Without the support, the tubing kinks and can seal during gamma irradiation. When the temperature sensor 405 is inserted it can puncture the tubing.

Figure 4:
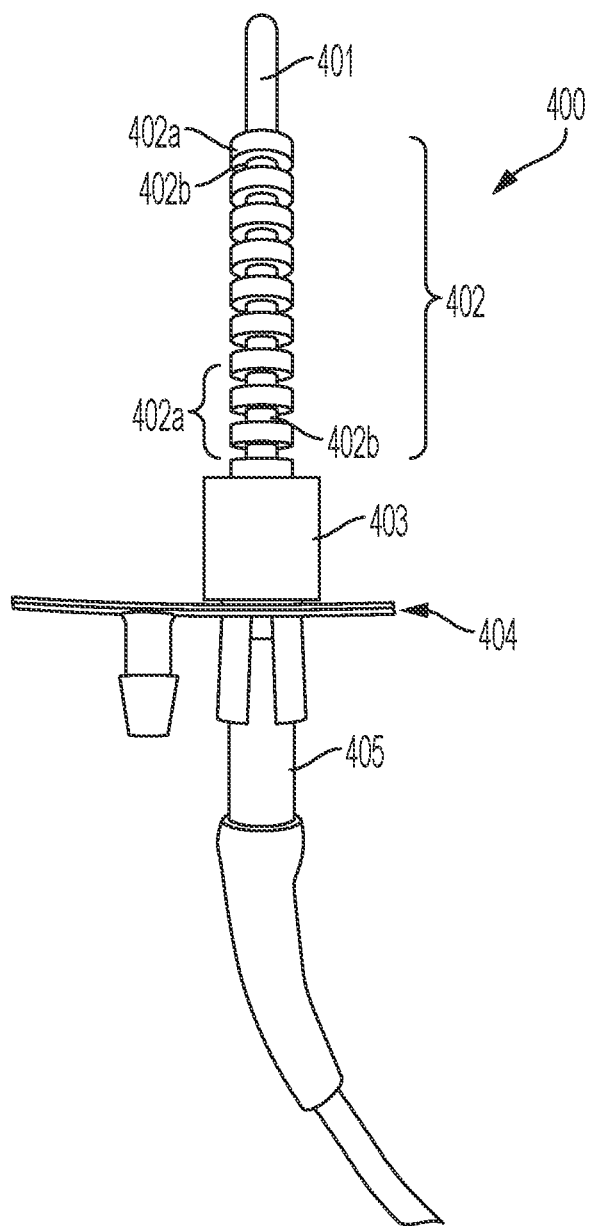
FIG. 4 shows a thermowell tube with a thermowell probe inserted therein according to an aspect of the invention.

In one embodiment shown in FIG. 4, a thermowell tube 400 includes a tip portion 401 and a reinforced portion 402. The tip portion 401 may have a length on the order of approximately 1 inch (2.54 cm), although the tip 401 may be longer or shorter depending on the needs of the user. The tip portion of the thermowell tube 400 is generally thinner than the reinforced portion 402 and is designed to allow enhanced heat flow from the interior portion of the bioreactor (not shown) to the thermowell distal tip 401 when it is inserted into the thermowell tube 400 as shown in FIG. 4. The reinforced portion 402 is defined by rib portions 402a that are spaced apart by separating portions 402b, in a spaced interval. The reinforced portion 402 provides greater structural stability for the thermowell tube 400.

The thermowell tube 400 may also comprise an optional base portion 403 that attaches to a thermowell flange 404, which may be used to form a seal with the bioreactor bag (not shown). Alternatively, the thermowell tube can be directly molded into the bioreactor bag. The base portion provide additional structural support for the thermowell when the thermowell is inserted into the thermowell tube 400.

Figure 5:
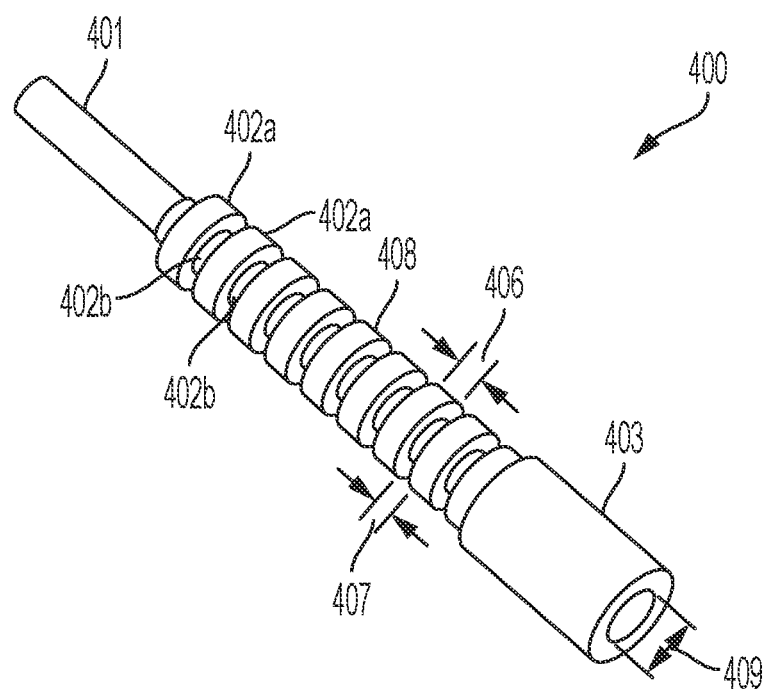
FIG. 5 shows a close-up perspective view of a thermowell tube according to an aspect of the invention.

FIG. 5 shows a close-up perspective view of the thermowell tube 400. The tip portion 401 of the thermowell tube 400 has a shape that maximizes the thermal exposure of the thermowell (not show) when inserted into the thermowell tube 400. The rib portions 402a are preferably present in a cylindrical configuration and are spaced apart by separating portions 402b, which may have the same geometry as the tip portion. In one aspect, the rib portion 402a are designed to have a length 406 and the separating portions 402b are designed to have a length 407. In a cylindrical configuration, the rib portions project outwardly to a height 408 that is defined by the difference in outer diameter of the rib portion 402a and the outer diameter of the separating portions 402b. The thermowell tube 400 has an inside diameter 409 that is adapted to closely match the outer diameter of the thermowell probe (not shown).

The reinforced portion 402 may be defined by several geometries in order to accomplish one or more objective of the invention. For example, in one variation, the height 408 of the rib portion 402a may progressively increase in a continuous or stepwise fashion in a direction from the tip portion 401 to the base portion 403. In some cases, the progressive increase in height 408 may result in a more continuous transition from the outer diameter of the tip portion 401 to the base portion 403. Other various reinforcement geometries are within the scope of the invention.

Figure 6:
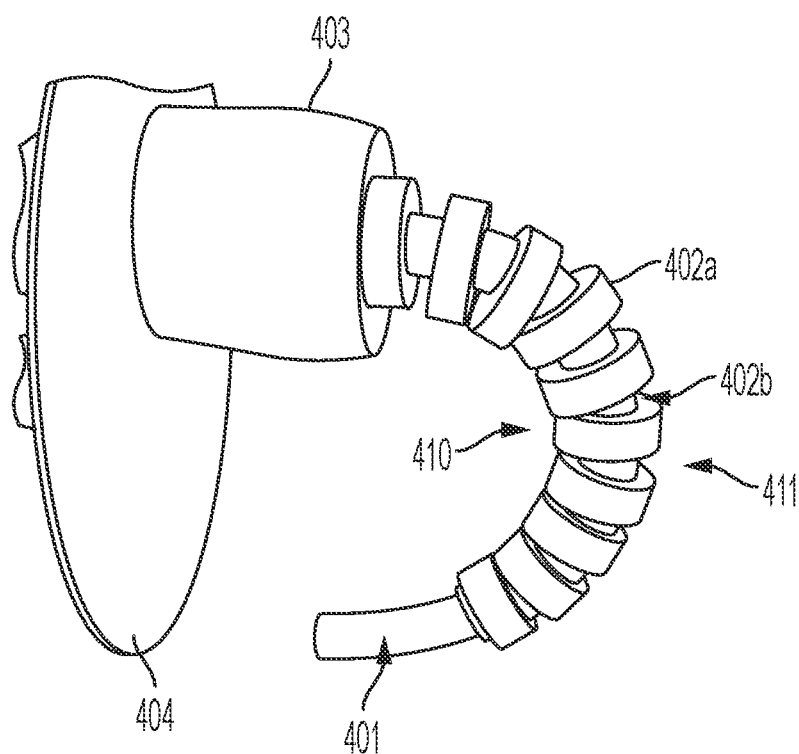
FIG. 6 shows the thermowell tube according to an aspect of the invention that is bent.

FIG. 6 shows the thermowell tube having a tip 401 and base 404 connected to a flange 404 that is being bent to illustrate the operation of the reinforced portion according to an aspect of the invention. The rib portions 402a toward the interior of the bend 410 may be configured to come into contact with each other to resist further deformation of the thermowell tube 400. In a preferred aspect, the contact between the rib portions 402a reinforces the entire structure when the tube is bent. This reinforcement protects the internal conduit 409 of the thermowell tube from collapse, crimping or other deformation. In this aspect, the length 407 of the spaced portion 402b between adjacent rib portions 402a is increased toward the exterior of the bend 411.

Figure 7:
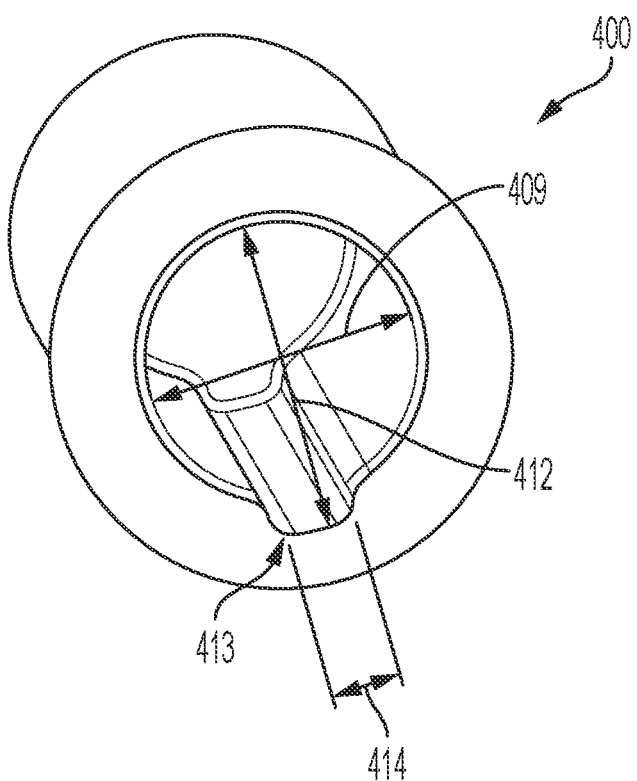
FIG. 7 shows a cross section of a portion of a thermowell tube according to an aspect of the invention.

FIG. 7 shows a cutout of the thermowell tube 400 showing the details of the inner diameter of the thermowell tube 400 according to an optional aspect of the invention. The thermowell tube 400 as discussed above has an interior diameter 409 that accommodates a cylindrical thermowell probe (not shown). In this aspect, the interior wall of the thermowell tube 400 is provided with a notch 413, wherein the inner diameter is increased to 412 for a length 414. The notch forms an internal channel which will allow air passage during insertion and removal of the sensor. The notch 413 allows air to escape from the interior of the thermowell tube 400 as the thermowell probe is inserted into the thermowell tube 400. It will be appreciated that the exact geometry of the notch can be varied in order to achieve one or more objectives of the invention. Also, the notch may be designed to run the entire length of the inner diameter of the thermowell cavity from the edge of the thermowell 400, or the edge of the optional thermowell base 403, all the way to the end of the thermowell tip 401. Alternatively, the notch may run over a defined portion of the interior diameter of the thermowell tube 400. In one aspect the notch 413 runs past the reinforced portion and terminates at some point in the tip portion 401. Alternatively, the notch 413 runs to the edge of the reinforced portion 402. In yet another aspect, the notch terminates at a point within the reinforced portion 402.

It should be appreciated that reinforced portion 402 described above with respect to a thermowell tube 400 may be applied to any other structure within a bioreactor or fermenter bag. The ribbing structure on the tubing can be applied to other applications on the single-use bioreactor bag where there is potential for the tubing to be kinked and shut down fluid flow. These areas include any internal tubing for fluid transfer, such as the internal sparge tubing or internal dip tubes that deliver fluid directly into the bulk process fluid. This can be used on the top of the bioreactor for the exhaust filter lines as these typical need to be bent in order to be contained and supported within the heaters while still providing a drain path for condensate back to the reactor. Any addition line that is supported and draped over a rigid bar could benefit from a small section of the ribbed tubing where the it is bent. This may prevent fattening of the tube which can cause flow restrictions and high-pressure events. As with the thermowell tube, these portions may be molded directly into the bag or attached to the bag using a flange as was shown with the thermowell above.

It should be appreciated that the reinforced tubing structure of the present invention will be particularly useful when added to a single use bioreactor. The ribbing along the tubing, e.g., a molded thermowell tube 400, prevents kinking and self-sealing due to gamma irradiation. When used with a thermowell probe, the temperature sensor portion of the probe is in the ~1 inch (~2.54 cm) section at the thermowell tube tip 401 and the thermowell tubing 400 will have a thin wall section to promote fast heat transfer response. An internal channel, or notch 413, will allow air passage during insertion and removal of temperature sensor 405.

Figure 1:
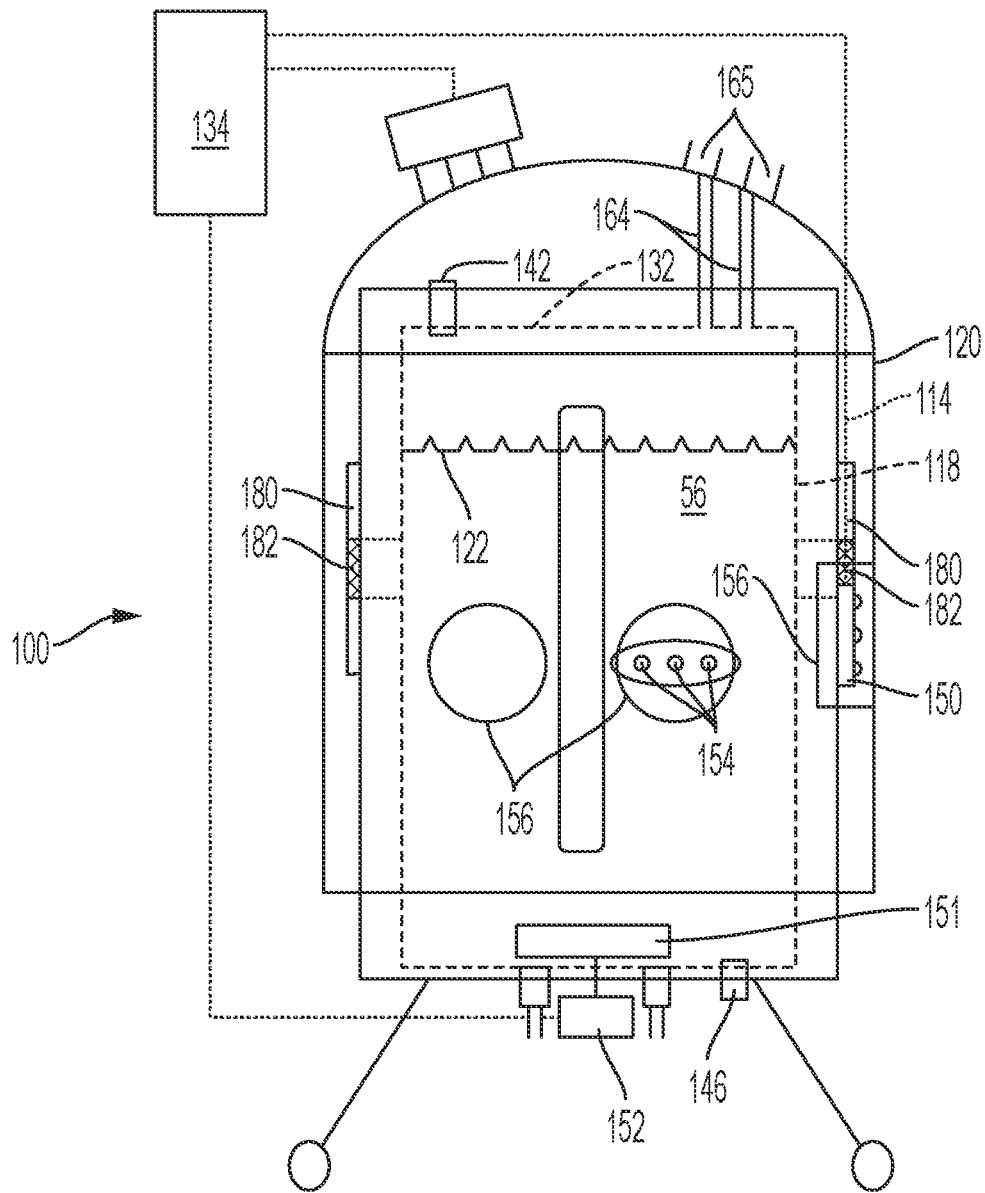
FIG. 1 shows an example of a prior art disposable large-scale bioreactor system.
Figure 2:
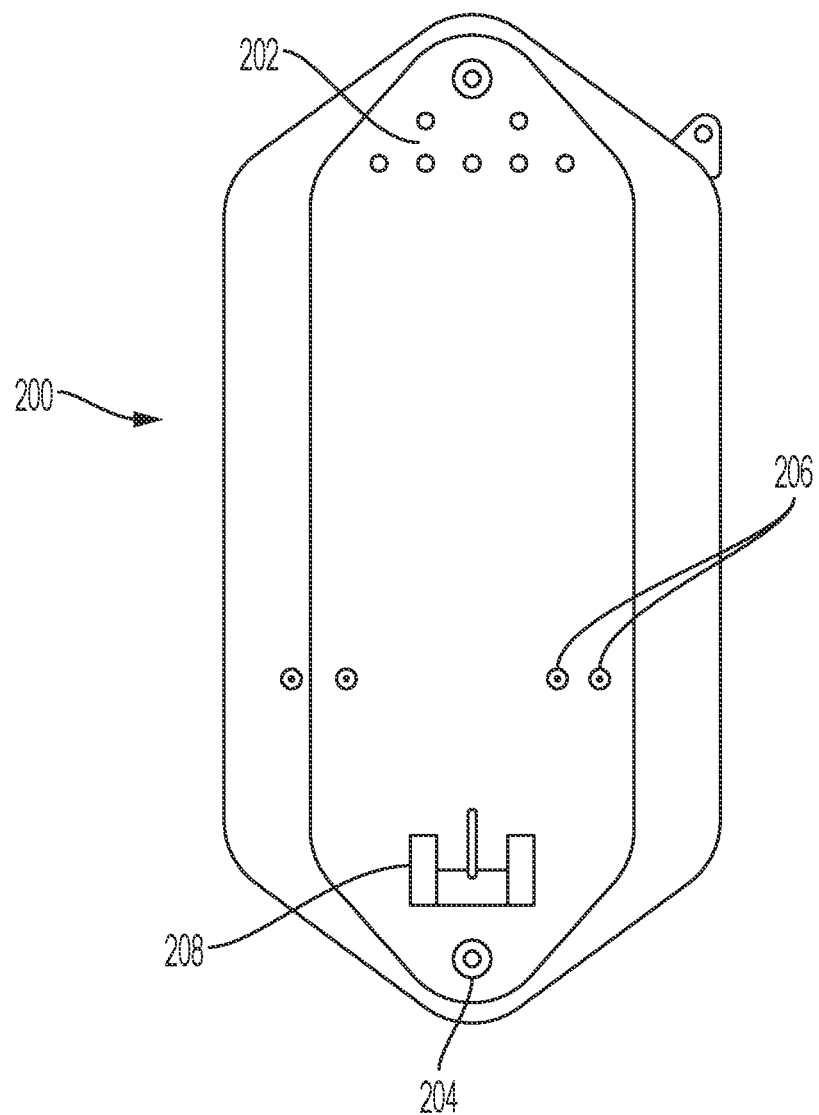
FIG. 2 shows an example of a prior art disposable bioreactor bag.
Figure 3:
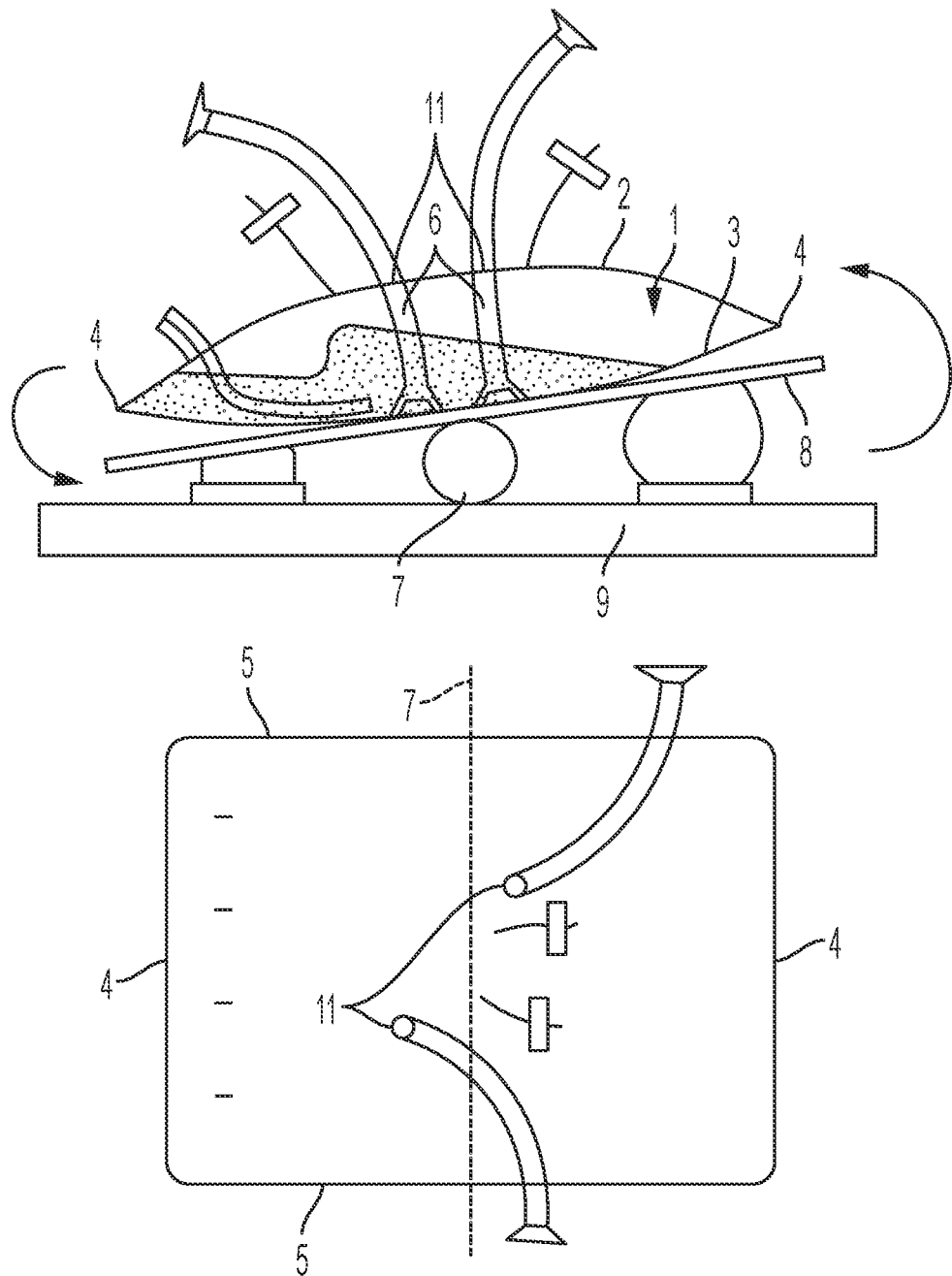
FIG. 3 shows an example of another prior art disposable bioreactor bag.

The reinforced tubular structures of the present invention, and particularly the reinforced thermowell tube, may be applied to any disposable bioprocess bag, and particularly those system made of flexible material such as plastics. Any of the disposable bags shown in FIGS. 1-3 may be modified to include internal tubular structures that are reinforced using embodiments of the present invention. In addition, any of the bags shown may be modified to include a reinforced thermowell tube in accordance with aspects of this invention.

Other embodiments and uses of the invention will be apparent to those skilled in the art from consideration of the specification and practice of the invention disclosed herein. All references cited herein, including all referenced patents and patent applications, are specifically and entirely hereby incorporated herein by reference where permissible. It is intended that the specification and examples be considered exemplary only, with the true scope and spirit of the invention indicated by the following claims.

The invention claimed is:

1. A bioprocess bag comprising:
 a bag wall defining an enclosed volume for holding biomaterials, the bag wall comprising at least one inlet port and at least one outlet port; and
 a tube structure comprising a first opened-end proximate the bag wall and a second distal end, the tube extending into the enclosed volume, and the tube structure comprising a reinforced portion proximate the first opened-end, wherein the reinforced portion comprises a ribbed structure.

2. The bioprocess bag of claim 1, wherein the second distal end is a closed-end, and the tube is adapted to accept a probe for measuring one or more properties of the biomaterials.

3. The bioprocess bag of claim 2, wherein the probe comprises a thermocouple or resistance temperature detector (RTD).

4. The bioprocess bag of claim 1, wherein the tube structure comprises a first opened-end proximate the bag wall and a second distal end extending into the enclosed volume, the reinforced portion proximate the first opened-end.

5. The bioprocess bag of claim 1, wherein the tube structure is adapted to accept a sparging wand.

6. The bioprocess bag of claim 1, wherein the ribbed structure comprises a pattern of sections that are raised relative to the tube outer surface, and the raised sections contacting each other when the tube structure is bent.

7. The bioprocess bag of claim 6, wherein the contact of the raised sections prevents crimping of the tube structure.

8. The bioprocess bag of claim 1, wherein the tube structure comprises a predominantly cylindrical inner wall, and a notch extending at least a portion of the length of the inner wall.

9. The bioprocess bag of claim 8, wherein the notch defines a channel that allows air to flow out when a probe is inserted into the tube structure.

10. The bioprocess bag of claim 1, wherein the bag wall comprises one or more of: an impeller, a heater, and/or a gas outlet.

11. A bioprocess bag comprising:
 a bag wall defining an enclosed volume for holding biomaterials, the bag wall comprising at least one inlet port and at least one outlet port; and
 a tube structure comprising a first opened-end proximate the bag wall and a second distal end, the tube extending into the enclosed volume, and the tube structure comprising a reinforced portion proximate the first opened-end, wherein the tube structure comprises a predominantly cylindrical inner wall, and a notch extending at least a portion of the length of the inner wall.

12. The bioprocess bag of claim 11, wherein the notch defines a channel that allows air to flow out when a probe is inserted into the tube structure.

13. The bioprocess bag of claim 11, wherein the second distal end is a closed-end, and the tube is adapted to accept a probe for measuring one or more properties of the biomaterials.

14. The bioprocess bag of claim 13, wherein the probe comprises a thermocouple or resistance temperature detector (RTD).

15. The bioprocess bag of claim 11, wherein the tube structure comprises a first opened-end proximate the bag wall and a second distal end extending into the enclosed volume, the reinforced portion proximate the first opened-end.

16. The bioprocess bag of claim 11, wherein the tube structure is adapted to accept a sparging wand.

17. The bioprocess bag of claim 11, wherein the ribbed structure comprises a pattern of sections that are raised relative to the tube outer surface, and the raised sections contacting each other when the tube structure is bent.

18. The bioprocess bag of claim 17, wherein the contact of the raised sections prevents crimping of the tube structure.

\* \* \* \* \*